United States Patent [19]
Olsen et al.

[11] Patent Number: 6,143,498
[45] Date of Patent: Nov. 7, 2000

[54] ANTIMICROBIAL PEPTIDE

[75] Inventors: Henrik S. Olsen, Gaithersburg; Steven M. Ruben, Olney, both of Md.

[73] Assignee: Human Genome Sciences, Inc., Rockville, Md.

[21] Appl. No.: 09/078,670

[22] Filed: May 14, 1998

Related U.S. Application Data

[60] Provisional application No. 60/046,415, May 14, 1997.

[51] Int. Cl.$^7$ .............................. C12Q 1/68; C07H 21/02
[52] U.S. Cl. ................................. 435/6; 536/22.1
[58] Field of Search ...................... 435/6, 69.1; 536/22.1

[56] References Cited

FOREIGN PATENT DOCUMENTS

| 44 27 531 | 2/1996 | Germany . |
| 196 29 119 | 6/1997 | Germany . |
| WO 94/26106 | 11/1994 | WIPO . |
| WO 97/22624 | 6/1997 | WIPO . |

OTHER PUBLICATIONS

Boman, H.G. and D. Hultmark, "Cell–Free Immunity in Insects," *Annu. Rev. Microbiol.* 41:103–126 (1987).

Boman, H.G., "Peptide Antibiotics and Their Role in Innate Immunity," *Annu. Rev. Immunol.* 13:61–92 (1995).

Diamond, G., et al., "Tracheal antimicrobial peptide, a cysteine–rich peptide from mammalian tracheal mucosa: Peptide isolation and cloning of a cDNA," *Proc. Natl. Acad. Sci. USA* 88:3952–3956 (1991).

Diamond, G., et al., "Airway epithelial cells are the site of expression of a mammalian antimicrobial peptide gene," *Proc. Natl. Acad. Sci. USA* 90:4596–4600 (1993).

Eisenhauer, P.B., et al., "Cryptdins: Antimicrobial Defensins of the Murine Small Intestine," *Infection and Immunity* 60:3556–3565 (1992).

Gabay, J.E., "Microbicidal mechanisms of phagocytes," *Curr. Opinion Immunol.* 1:36–40 (1988).

Gabay, J.E., et al., "Antibiotic proteins of human polymorphonuclear leukocytes," *Proc. Natl. Acad. Sci. USA* 86:5610–5614 (1989).

Ganz, T., et al., "Defensins, Natural Peptide Antibiotics of Human Neutrophils," *J. Clin. Invest.* 76:1427–1435 (1985).

Ganz, T., "Extracellular Release of Antimicrobial Defensins by Human Polymorphonuclear Leukocytes," *Infection and Immunity* 55:568–571 (1987).

Ganz, T., et al., "The Structure of the Rabbit Macrophage Defensin Genes and Their Organ–Specific Expression," *J. Immunol.* 143:1358–1365 (1989).

Harder, J., et al., "A peptide antibiotic from human skin," *Nature* 387:861 (Jun. 1997).

Jones, D.E., and C.L. Bevins, "Paneth Cells of the Human Small Intestine Express an Antimicrobial Peptide Gene," *J. Biol. Chem.* 267:23216–23225 (1992).

Lehrer, R. I., et al., "Defensins: Antimicrobial and Cytotoxic Peptides of Mammalian Cells," *Annu. Rev. Immunol.* 11:105–128 (1993).

Schonwetter, B.S., et al., "Epithelial Antibiotics Induced at Sites of Inflammation," *Science* 267:1645–1648 (1995).

Selsted, M.E., et al., "Enteric Defensins: Antibiotic Peptide Components of Intestinal Host Defense," *J. Cell. Biol.* 118:929–936 (1992).

Soravia, E., et al., "Antimicrobial properties of peptides from Xenopus granular gland secretions," *FEBS Letters* 228:337–340 (1988).

Zasloff, M., "Magainins, a class of antimicrobial peptides from Xenopus skin: Isolation, characterization of two active forms, and partial cDNA sequence of a precursor," *Proc. Natl. Acad. Sci. USA* 84:5449–5453 (1987).

NCBI Entrez, GenBank Report, Accession No. Z71389, from Harder, J. (Jul. 1997).

Dialog File 351, Accession No. 199611, Derwent WPI English language abstract for De 44 27 531.

Dialog File 351, Accession No. 199730, Derwent WPI English language abstract for DE 196 29 119.

*Primary Examiner*—Eggerton A. Campbell
*Attorney, Agent, or Firm*—Sterne, Kessler, Goldstein & Fox P.L.L.C.

[57] ABSTRACT

The present invention relates to a novel human antimicrobial peptide which is a member of the defensin superfamily. In particular, isolated nucleic acid molecules are provided encoding the human antimicrobial peptide. Antimicrobial peptide are also provided as are vectors, host cells and recombinant methods for producing the same. Also provided are diagnostic methods for detecting disorders related to the immune system and therapeutic methods for such disorders.

122 Claims, 5 Drawing Sheets

```
    GACTCAGCTCCTGGTGAAGCTCCCAGCCATCAGCCATGAGGGTCTTGTATCTCCTCTTCT
  1 ---------+---------+---------+---------+---------+---------+  60
                                    MetArgValLeuTyrLeuLeuPheS
                                     M   R   V   L   Y   L   L   F   S

CGTTCCTCTTCATATTCCTGATGCCTCTTCCAGGTGTTTTTGGTGGTATAGGCGATCCTG
 61 ---------+---------+---------+---------+---------+---------+ 120
    erPheLeuPheIlePheLeuMetProLeuProGlyValPheGlyGlyIleGlyAspProV
     F   L   F   I   F   L   M   P   L   P   G   V   F   G   G   I   G   D   P   V

TTACCTGCCTTAAGAGTGGAGCCATATGTCATCCAGTCTTTTGCCCTAGAAGGTATAAAC
121 ---------+---------+---------+---------+---------+---------+ 180
    alThrCysLeuLysSerGlyAlaIleCysHisProValPheCysProArgArgTyrLysG
       T   C   L   K   S   G   A   I   C   H   P   V   F   C   P   R   R   Y   K   Q

AAATTGGCACCTGTGGTCTCCCTGGAACAAAATGCTGCAAAAAGCCATGAGGAGGCCAAG
181 ---------+---------+---------+---------+---------+---------+ 240
    lnIleGlyThrCysGlyLeuProGlyThrLysCysCysLysLysProEnd
        I   G   T   C   G   L   P   G   T   K   C   C   K   K   P   *

AAGCTGCTGTGGCTGATGCGGATTCAGAAAGGGCTCCCTCATCAGAGACGTGCGACATGT
241 ---------+---------+---------+---------+---------+---------+ 300

AAACCAAATTAAACTATGGTGTC
301 ---------+---------+--- 323
```

FIG.1

```
1  MRVLYLLFSFLFIFLMPLPGVFGGIGDPVTCLKSGAICHPVFCPRRYKQIGTCGLPGTKC  60
   MR+ +LL + LF+ L    G   G+G+PV+C+++  IC P+ CP   KQIGTC      KC
1  MRLHHLLLALLFLVLSAWSGFTQGVGNPVSCVRNKGICVPIRCPGSMKQIGTCVGRAVKC  60

61 CKK 63
   C+K
61 CRK 63
```

FIG.2

1  AAGCTT AAAAAAACTGCAAAAAAATAGT TTGACTTGTGAGCGGATAACAAT
                                 -35   Operator 1

Operator 2
     ATTGTGAGCGGATAACAAT TCACACATTAA

50 TAAGATGTACCCAA
      -10
           S/D
94 AGAGGAGAAAATTA CATATG

FIG. 5

ANTIMICROBIAL PEPTIDE

This application claims the benefit of the filing date of provisional application Ser. No. 60/046,415 filed on May 14, 1997, which is herein incorporated in its entirety.

BACKGROUND OF THE INVENTION

1. Field of the Invention

The present invention relates to a novel human defensin peptide. More specifically, isolated nucleic acid molecules are provided encoding a human antimicrobial peptide. Antimicrobial polypeptides are also provided, as are vectors, host cells and recombinant methods for producing the same. Also provided are diagnostic methods for detecting disorders related to the immune system and therapeutic methods for treating such disorders.

2. Related Art

One of the key roles of the respiratory epithelium in mammals is to form a barrier to potentially harmful environmental threats. A number of defense mechanisms have been identified that protect the respiratory tract from airborne agents that are thought to be responsible for airway disease, such as infectious agents, gases and particulates. (Newhouse et al., "Respiratory Tract Defense Mechanism" *Textbook of Pulmonary Disease,* Little Brown and Co. (1989)). The recent identification and characterization of antimicrobial peptides from a variety of species has unveiled a new member of the animal host defense system and are believed to participate in the defense against potential microbial pathogens. These newly identified antimicrobial peptides families include cecropins, magainins, and defensins. Cecropins were the first well-characterized family of structurally related antimicrobial polypeptides and are found in a wide distribution of insects. (Bowman et al., *Ann. Rev. of Microbiol.* 41:103 (1987)). In vertebrates, the magainin family of antimicrobial peptides have been isolated from the glands of the skin and gastrointestinal tract of *Xenopus laevis,* and are thought to form the basis for defense system of the amphibian mucosal surfaces against infection. (Soravia et al., *FEBS Lett.* 228:337 (1988); Zasloff et al., *Proc. Natl. Acad. Sci.* 84:5449 (1987)). Defensins are antimicrobial peptides found in phagocytic cells isolated from several mammalian species including man and may be characterized by eight invariant residues within the sequence. (Gabay et al., *Curr. Opin. Immunol.* 1: 36 (1988); Gabay et al., *Proc. Natl. Acad. Sci.* 86:5610 (1989); Ganz et al., *Infect. Immun.* 55:568 (1987); Ganz et al., *J. Immunol.* 143:1358 (1989); Ganz et al., *J. Clin. Invest.* 76:1427 (1985)).

The mechanism of antimicrobial activity of peptides such as the defensins is via a selective membrane disruption leading to a characteristic broad spectrum of antibiotic activity. (Bowman, *Ann. Rev. of Immunol.* 13:61 (1995)). The antimicrobial spectrum of defensins includes gram positive and gram negative bacteria, mycobacteria, *T. pallidum,* many fungi, some enveloped-viruses. (Bowman, *Ann. Rev. of Immunol.* 13:61 (1995)). Defensins exert non-specific cytotoxic activity against a wide range of normal and malignant targets, including cells resistant to TNF-α and NK-cytolytic factor. They appear to kill mammalian target cells and microorganisms by common mechanism which involves initial electrostatic interactions with negatively charged target cell surface molecules, followed by insertion into the cell membranes which they permneabilize, forming voltage regulated channels. (Lehrer et al., *Ann. Rev. of Immunol.* 11:105 (1993)).

In addition to their antimicrobial and cytotoxic properties, some defensins act as opsonins, while others inhibit protein kinase C, bind specifically to the ACTH receptor and block steroidogenesis or act as selective chemoattractins for monocytes. Defensins are newly delineated family of effector molecules whose contribution to host cell defense, inflammation, and cytotoxicity may be considerable for humans. (Lehrer et al., *Ann. Rev. of Immunol.* 11:105 (1993)).

Defensins are basic peptides 30–34 amino acids with three disulfide bonds. The known characterized defensins for both myeloid and nonmyeloid tissues all have highly conserved amino acid residues within the family, including 6 invariant cysteins. Recent studies have found that similar antimicrobial peptides are also made by certain epithelial cells suggesting an additional role in the defense of mucosal surfaces. (Diamond et al., *Proc. Natl. Acad. Sci.* 90:5496 (1993); Diamond et al., *Proc. Natl. Acad. Sci.* 88:3952 (1991); Eisenhauer et al., *Infect. Immun.* 60:3556 (1992); Jones et al., *J. Biol. Chem.* 267:23216 (1992); Schonwetter et al., *Science* 267:1645 (1995); Selsted et al., *J. Cell. Biol.* 118:929 (1992)).

Tracheal antimicrobial peptide (TAP) is a 38 amino acid peptide isolated from the bovine respiratory mucosa and was the first member of what is now recognized as arelatively large family of antimicrobial peptides, β-defensin, all of which have broad spectrum antimicrobial activity in vitro. (Diamond et al., *Proc. Natl. Acad. Sci.* 88:3952 (1991)). Recently a second β-defensins of epithelial origin, lingual antimicrobial peptide (LAP) was isolated from bovine tongue. (Schonwetter et al., *Science* 267:1645 (1995); Selsted et al., *J. Cell. Biol.* 118:929 (1992)).

Thus, there is a need for polypeptides that function as antimicrobial or immune regulators, since disturbances of such regulation may be involved in disorders relating to infectious diseases, inflamrnation and immune disorders.

SUMMARY OF THE INVENTION

The present invention provides isolated nucleic acid molecules comprising a polynucleotide encoding the antimicrobial polypeptide having the amino acid sequence shown in SEQ ID NO:2 or the amino acid sequence encoded by the cDNA clone deposited as ATCC Deposit Number 97982 on Apr. 14, 1997.

The present invention also relates to recombinant vectors, which include the isolated nucleic acid molecules of the present invention, and to host cells containing the recombinant vectors, as well as to methods of making such vectors and host cells and for using them for production of antimicrobial polypeptides or peptides by recombinant techniques.

The invention further provides an isolated human antimicrobial polypeptide having an amino acid sequence encoded by a polynucleotide described herein.

The invention provides a diagnostic method useful during diagnosis of immune system disorders.

An additional aspect of the invention is related to a method for treating an individual in need of an increased level of antimicrobial peptide activity in the body comprising administering to such an individual a composition comprising a therapeutically effective amount of an isolated antimicrobial peptide of the invention or an agonist thereof.

A still further aspect of the invention is related to a method for treating an individual in need of a decreased level of antimicrobial peptide activity in the body comprising, administering to such an individual a composition comprising a therapeutically effective amount of an antimicrobial peptide antagonist.

BRIEF DESCRIPTION OF THE FIGURES

FIG. 1 shows the nucleotide (SEQ ID NO:1) and deduced amino acid (SEQ ID NO:2) sequences of human antimicrobial peptide. The protein has a leader sequence of about 23 amino acid residues (underlined) and a deduced molecular weight of about 7.3 kDa. The underlined amino acids residues in FIG. 1 (i.e., the first 23 amino acids) correspond to amino acids −23 to −1 in SEQ ID NO:2. The next 41 amino acids (not underlined) in FIG. 1 correspond to amino acids 1 to 41 in SEQ ID NO:2.

FIG. 2 shows the regions of similarity between the amino acid sequences of the antimicrobial peptide protein and bovine tracheal antimicrobial peptide (SEQ ID NO:3).

FIG. 5 shows the nucleotide sequence of the regulatory elements of the pHE4a promoter (SEQ ID NO:5). The two lac operator sequences, the Shine-Delgarno sequence (S/D), and the terminal HindIII and NdeI restriction sites (italicized) are indicated.

DETAILED DESCRIPTION

Figure 3:
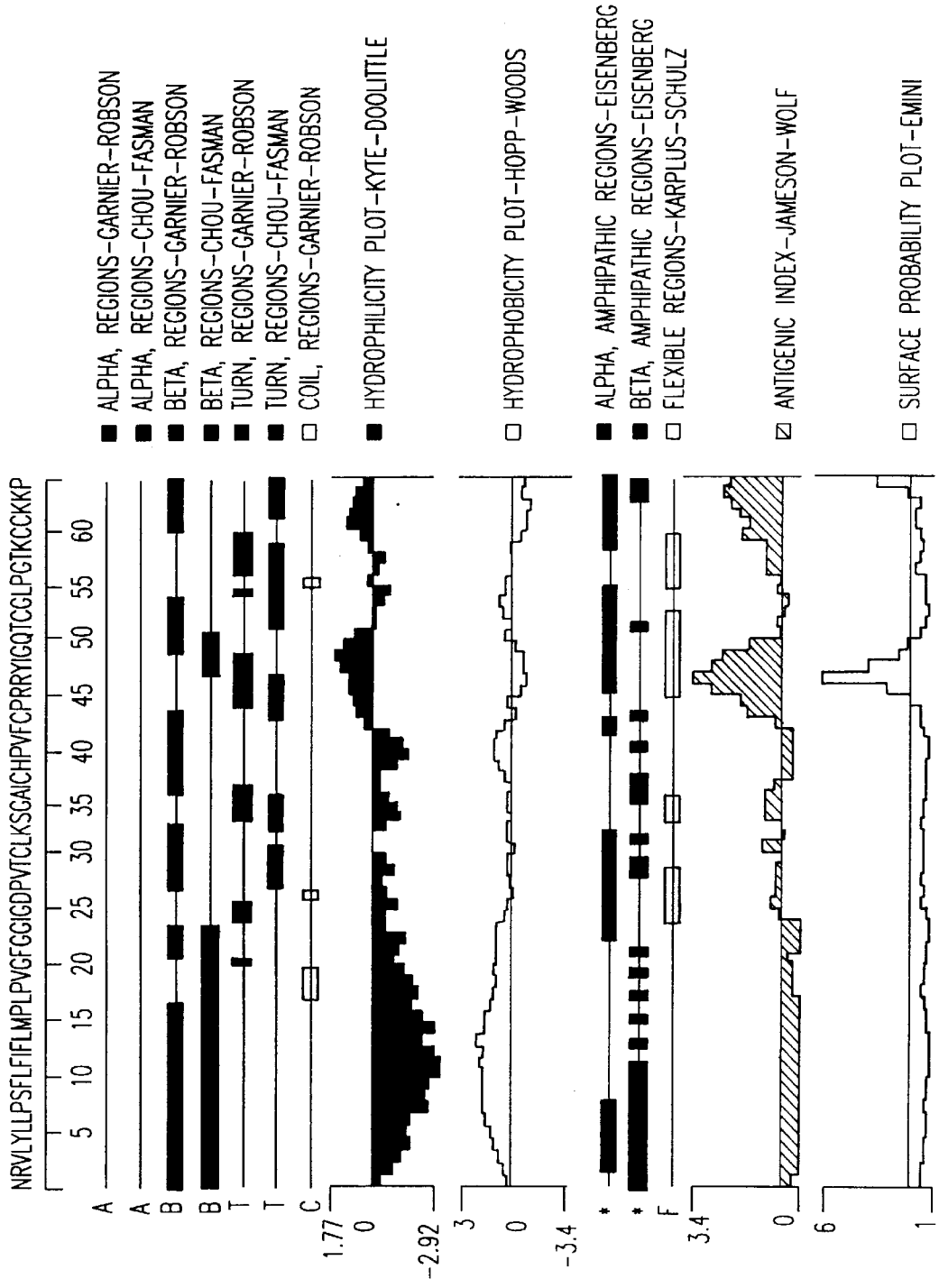
FIG. 3 shows an analysis of the antimicrobial peptide amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 42 to about 50, and about 54 to about 64 in FIG. 1 correspond to the shown highly antigenic regions of the antimicrobial peptide protein. These highly antigenic fragments in FIG. 1 correspond to the following fragments, respectively, in SEQ ID NO:2: amino acid residues about 19 to about 27, and about 31 to about 41.

The present invention provides isolated nucleic acid molecules comprising a polynucleotide encoding an antimicrobial peptide having the amino acid sequence shown in SEQ ID NO:2, which was determined by sequencing a cloned cDNA. The antimicrobial peptide of the present invention shares sequence homology with bovine tracheal antimicrobial peptide (FIG. 2) (SEQ ID NO:3).

The nucleotide sequence shown in SEQ ID NO:1 was obtained by sequencing a cDNA clone (HLJB 175), which was deposited on Apr. 14, 1997 at the American Type Culture Collection, Patent Depository, 10801 University Boulevard, Manassas, Va. 20110-2209, and given accession number 97982. The deposited clone is inserted in the pCM-VSport1 using the SalI/NotI restriction endonuclease cleavage sites. Nucleic Acid Molecules Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO: 1, a nucleic acid molecule of the present invention encoding a antimicrobial peptide polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from lung tissue. The determined nucleotide sequence of the antimicrobial peptide cDNA of SEQ ID NO: 1 contains an open reading frame encoding a protein of about 64 amino acid residues, a predicted leader sequence of about 23 amino acid residues, and a deduced molecular weight of about 7.3 kDa. The antimicrobial peptide shown in SEQ ID NO:2 is about 44% identical and about 63% similar to bovine tracheal antimicrobial peptide (FIG. 2).

The present invention also provides the mature form(s) of the antimicrobial peptide protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells A4 and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature antimicrobial peptide polypeptides having the amino acid sequence encoded by the cDNA clone contained in the plasmid identified as ATCC Deposit No. 97982 and as shown in SEQ ID NO:2. By the mature antimicrobial peptide having the amino acid sequence encoded by the cDNA clone contained in the plasmid identified as ATCC Deposit 97982is meant the mature form(s) of the antimicrobial peptide produced by expression in a mammalian cell (e.g., COS cells, as described below) of the complete open reading frame encoded by the human DNA sequence of the clone contained in the vector in the deposited. As indicated below, the mature antimicrobial peptide having the amino acid sequence encoded by the cDNA clone contained in ATCC Deposit No. 97982 may or may not differ from the predicted "mature" antimicrobial peptide shown in SEQ ID NO:2 (amino acids from about 1 to about 23) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete antimicrobial peptide polypeptides of the present invention were analyzed by a computer program ("PSORT") (K .Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the antimicrobial peptide protein is predicted to consist of amino acid residues from about −23 to about −1 in SEQ ID NO:2, while the mature antimicrobial peptide protein is predicted to consist of residues from about 1 to about 41 in SEQ ID NO:2.

As one of ordinary skill would appreciate, due to the possibilities of sequencing errors, as well as the variability of cleavage sites for leaders in different known proteins, the predicted antimicrobial peptide polypeptide encoded by the deposited cDNA comprises about 64 amino acids, but may be anywhere in the range of 55–75 amino acids; and the predicted leader sequence of this protein is about 23 amino acids, but may be 20, 21, 22, 24 or 25 amino acids in length.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO: 1; DNA molecules comprising the coding sequence for the mature antimicrobial peptide protein; and DNA molecules which comprise a sequence substantially different from those described above but which, due to the degeneracy of the genetic code, still encode the antimicrobial peptide protein. Of course, the genetic code is well known in the art. Thus, it would be routine for one skilled in the art to generate such degenerate variants.

In another aspect, the invention provides isolated nucleic acid molecules encoding the antimicrobial peptide polypeptide having an amino acid sequence as encoded by the cDNA clone contained in the plasmid deposited as ATCC Deposit No. 97982 on Apr. 14, 1997. In a further embodiment, nucleic acid molecules are provided encoding the mature antimicrobial peptide polypeptide or the full-length antimicrobial peptide polypeptide lacking the N-terminal methionine. The invention also provides an isolated nucleic acid molecule having the nucleotide sequence shown in SEQ ID NO: 1 or the nucleotide sequence of the antimicrobial peptide cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the antimicrobial peptide gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIG. 1 (SEQ ID NO: 1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, or 323 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

Preferred nucleic acid fragments of the present invention include nucleic acid molecules encoding epitope-bearing portions of the antimicrobial peptide protein. In particular, such nucleic acid fragments ofthe present invention include nucleic acid molecules encoding: a polypeptide comprising amino acid residues from about 19 to about 27 in SEQ ID NO:2; and a polypeptide comprising amino acid residues from about 31 to about 41 in SEQ ID NO:2. The inventors have determined that the above polypeptide fragments are antigenic regions of the antimicrobial peptide protein. Methods for determining other such epitope-bearing portions of the antimicrobial peptide protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97982. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5x Denhardtfs solution, 10% dextran sulfate, and 20 µg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO: 1). Of course, a polynucleotide which hybridizes only to a poly A sequence (such as the 3' terminal poly(A) tract of the antimicrobial peptide cDNA shown in SEQ ID NO: 1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a antimicrobial peptide polypeptide may include, but are not limited to those encoding the amino acid sequence of the mature polypeptide, by itself; the coding sequence for the mature polypeptide and additional sequences, such as those encoding the about 23 amino acid leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3, sequences, such as the transcribed, non-translated sequences that play a role in transcription, mRNA processing, including splicing and polyadenylation signals, for example - ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in apQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 3 7: 767 (1984). As discussed below, other such fusion proteins include the antimicrobial peptide fused to Fc at the N- or C-terminus.

The present invention further relates to variants of the nucleic acid molecules of the present invention, which encode portions, analogs or derivatives of the antimicrobial peptide protein. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the antimicrobial peptide protein or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine, (c) a nucleotide sequence encoding the polypeptide having the amino acid sequence at positions from about 1 to about 41 in SEQ ID NO:2; (d) a nucleotide sequence encoding the polypeptide having the amino acid sequence encoded by the cDNA clone contained in ATCC Deposit No. 97982; (e) a nucleotide sequence encoding the mature antimicrobial peptide polypeptide having the amino acid sequence encoded by the cDNA clone contained in ATCC Deposit No. 97982; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding an antimicrobial peptide is intended that the nucleotide sequence of the polynucleotide is identical to the reference sequence except that the polynucleotide sequence may include up to five point mutations per each 100 nucleotides of the reference nucleotide sequence encoding the antimicrobial peptide polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO: 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO: 1 or to the nucleic acid sequence of the deposited cDNA, irrespective of whether they encode a polypeptide having antimicrobial peptide activity. This is because even where a particular nucleic acid molecule does not encode a polypeptide having antimicrobial peptide activity, one of skill in the art would still know how to use the nucleic acid molecule, for instance, as a hybridization probe or a polymerase chain reaction (PCR) primer. Uses of the nucleic acid molecules of the present invention that do not encode a polypeptide having antimicrobial peptide activity include, inter alia, (1) isolating the antimicrobial peptide gene or allelic variants thereof in a cDNA library; (2) in situ hybridization (e.g., "FISH") to metaphase chromosomal spreads to provide precise chromosomal location of the antimicrobial peptide gene, as described in Verma et al., *Human Chromosomes: A Manual of Basic Techniques,* Pergamon Press, New York (1988); and Northern Blot analysis for detecting antimicrobial peptide mRNA expression in specific tissues.

Preferred, however, are nucleic acid molecules having sequences at least 95%, 96%, 97%, 98% or 99% identical to a nucleic acid sequence shown in SEQ ID NO: 1 or to a nucleic acid sequence of the deposited cDNA which do, in fact, encode a polypeptide having antimicrobial peptide protein activity. By "a polypeptide having antimicrobial peptide activity" is intended polypeptides exhibiting antimicrobial peptide activity in a particular biological assay. For example, antimicrobial peptide activity can be measured using, for example, the antimicrobial assay as described in Diamond et al., *Proc. Natl. Acad. Sci.* 88:3952 (1991). Briefly, a concentrated aliquot of the candidate antimicrobial peptide is spotted onto a lawn of *E. coli* and is incubated overnight at 37° C. Minimal inhibitory concentration of the peptide is determined by a modification of the method described by Soravia et al. *FEBS Lett.* 228: 337–340(1988). Briefly, $2.5 \times 10^4$ bacteria are incubated with increasing concentrations of the peptide in static 96-well microtiter plates overnight at 37° C. Bacterial growth is assessed by optical density measurments at 600 nm. Control incubations in the absence of peptide and incubations in the absence of bacteria serve to set baseline values.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence of the deposited cDNA or a nucleic acid sequence shown in SEQ ID NO: 1 will encode a polypeptide "having antimicrobial peptide protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having antimicrobial peptide protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of antimicrobial peptide polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli,* Streptomyces and *Salmonella typhimurium* cells; fingal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 4:
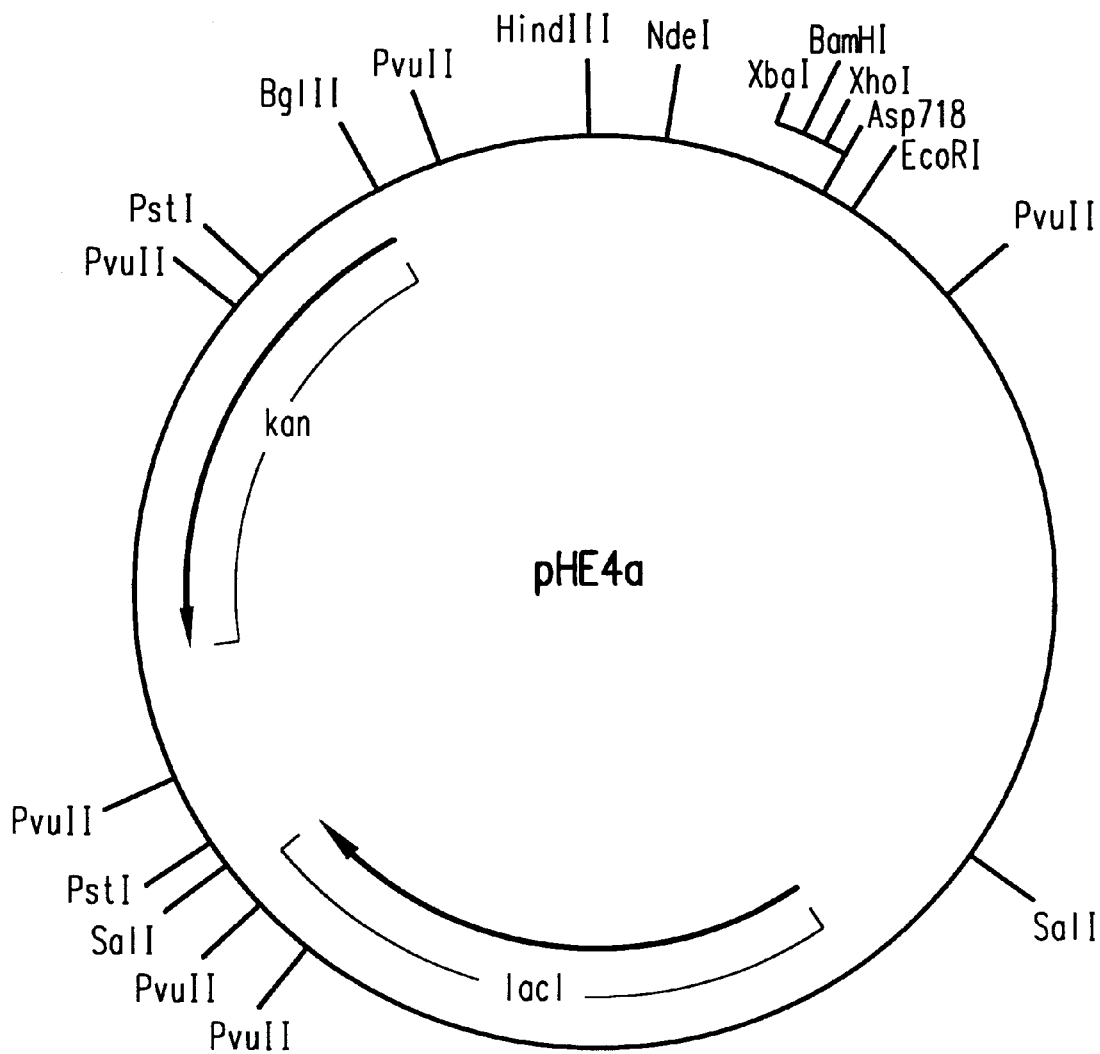
FIG. 4 shows a schematic representation of the pHE4a expression vector (SEQ ID NO:4). The locations of the kanamycin resistance marker gene, the multiple cloning site linker region, the oriC sequence, and the lacIq coding sequence are indicated.

As summarized in FIGS. 4 and 5, components of the pHE4a vector (SEQ ID NO:4) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC 19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. The pHE4a vector was deposited with the ATCC on Feb. 25, 1998, and given accession number 209645.

A nucleotide sequence encoding antimicrobial polypeptide (SEQ ID NO:1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding antimicrobial polypeptide (SEQ ID NO:1) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac perator. Amann, E. et al., *Gene* 69:301–315 (1988); Stark, M., *Gene* 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG).antimicrobial polypeptide thus is not produced in appreciable quantities in uninduced host cells containing the pHE4a vector. Induction of these host cells by the addition of an agent such as IPTG, however, results in the expression of the antimicrobial polypeptide coding sequence.

The promoter/operator sequences of the pHE4a vector (SEQ ID NO:5) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4a vector except for the antimicrobial polypeptide coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4avector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:4).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The antimicrobial peptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Human Antimicrobial Polypeptides and Fragments

The invention further provides an isolated antimicrobial peptide having the amino acid sequence encoded by the deposited cDNA, or the amino acid sequence in SEQ ID NO:2, or a peptide or polypeptide comprising a portion of the above polypeptides.

It will be recognized in the art that some amino acid sequences of the antimicrobial peptide can be varied without significant effect of the structure or function of the protein. If such differences in sequence are contemplated, it should be remembered that there will be critical areas on the protein which determine activity.

Thus, the invention further includes variations of the antimicrobial peptide which show substantial antimicrobial peptide activity or which include regions of antimicrobial peptide such as the protein portions discussed below. Such mutants include deletions, insertions, inversions, repeats, and type substitutions. As indicated above, guidance concerning which amino acid changes are likely to be phenotypically silent can be found in Bowie, J.U., et al., "Deciphering the Message in Protein Sequences: Tolerance to Amino Acid Substitutions," Science 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the antimicrobial peptide. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331–340 (1967); Robbins et al., Diabetes 36:838–845 (1987); Cleland et al. Crit. Rev. Therapeutic Drug Carrier Systems 10:307–377 (1993)).

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |

TABLE 1-continued

| Conservative Amino Acid Substitutions. | |
|---|---|
| Small | Alanine |
|  | Serine |
|  | Threonine |
|  | Methionine |
|  | Glycine |

Of course, the number of amino acid substitutions a skilled artisan would make depends on many factors, including those described above. Generally speaking, the number of amino acid substitutions for any given antimicrobial polypeptide will not be more than 50, 40, 30, 20, 10, 5, or 3.

Amino acids in the antimicrobial peptide of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

The polypeptides of the present invention are preferably provided in an isolated form. By "isolated polypeptide" is intended apolypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the antimicrobial peptide polypeptide can be substantially purified by the one-step method described in Smith and Johnson, Gene 67:31–40 (1988).

The polypeptides ofthe present invention include the polypeptide encoded by the deposited cDNA including the leader, the mature polypeptide encoded by the deposited cDNA minus the leader (i.e., the mature protein), a polypeptide comprising amino acids about −23 to about 41 in SEQ ID NO:2; a polypeptide comprising amino acids about −22 to about 41 in SEQ ID NO:2; a polypeptide comprising amino acids about 1 to about 41 in SEQ ID NO:2; as well as polypeptides which are at least 95% identical, still more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a antimicrobial peptide is intended that the amino acid sequence of the polypeptide is identical to the reference sequence except that the polypeptide sequence may include up to five amino acid alterations per each 100 amino acids of the reference amino acid of the antimicrobial peptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate antimicrobial peptide-specific antibodies include: a polypeptide comprising amino acid residues from about 19 to about 27 in SEQ ID NO:2; and a polypeptide comprising amino acid residues from about 31 to about 41 in SEQ ID NO:2. As indicated above, the inventors have determined that the above polypeptide fragments are antigenic regions of the antimicrobial peptide protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci USA* 82:5131–5135. This "Simultaneous Multiple Peptide Synthesis (SMPS)" process is further described in U.S. Pat. No. 4,631,211 to Houghten et al. (1986).

As one of skill in the art will appreciate, antimicrobial peptide polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86(1988)). Fusionproteins that have a disulfide-linked dimeric structure due to the IgG part can also be more efficient in binding and neutralizing other molecules than the monomeric antimicrobial peptide protein or protein fragment alone (Fountoulakis et al., *J. Biochem* 270:3958–3964 (1995)).

Diagnosis

The present inventors have discovered that the antimicrobial peptide of the present invention is expressed in lung lymph node and corneatissues. It is believe that for a number of immune system-related disorders, substantially altered (increased or decreased) levels of antimicrobial peptide gene expression can be detected in immune system tissue or other cells or bodily fluids (e.g., sera, plasma, urine, synovial fluid or spinal fluid) taken from an individual having such a disorder, relative to a "standard" antimicrobial peptide gene expression level, that is, the antimicrobial peptide expression level in immune system tissues or bodily fluids from an individual not having the immune system disorder. Thus, the invention provides a diagnostic method useful during diagnosis of a immune system disorder, which involves measuring the expression level of the gene encoding the antimicrobial peptide protein in immune system tissue or other cells or body fluid from an individual and comparing the measured gene expression level with a standard antimicrobial peptide gene expression level, whereby an increase or decrease in the gene expression level compared to the standard is indicative of an immune system disorder.

In particular, it is believed that certain tissues in mammals with cancer of the lung lymph node or cornea express significantly enhanced or reduced levels of the antimicrobial peptide protein and mRNA encoding the antimicrobial peptide protein when compared to a corresponding "standard" level. Further, it is believed that enhanced levels of the antimicrobial peptide protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a immune system disorder, including cancers of this system which involves measuring the expression level of the gene encoding the antimicrobial peptide protein in immune system tissue or other cells or body fluid from an individual and comparing the measured gene expression level with a standard antimicrobial peptide gene expression level, whereby an increase or decrease in the gene expression level compared to the standard is indicative of an immune system disorder.

Where a diagnosis of a disorder in the immune system has already been made according to conventional methods, the present invention is useful as a prognostic indicator, whereby patients exhibiting depressed antimicrobial peptide gene expression will experience a worse clinical outcome relative to patients expressing the gene at a level nearer the standard level.

By "assaying the expression level of the gene encoding the antimicrobial peptide" is intended qualitatively or quantitatively measuring or estimating the level of the antimicrobial peptide or the level of the mRNA encoding the antimicrobial peptide in a first biological sample either directly (e.g., by determining or estimating absolute protein level or mRNA level) or relatively (e.g., by comparing to the antimicrobial peptide level or mRNA level in a second biological sample). Preferably, the antimicrobial peptide protein level or mRNA level in the first biological sample is measured or estimated and compared to a standard antimicrobial peptide protein level or mRNA level, the standard being taken from a second biological sample obtained from an individual not having the disorder or being determined by averaging levels from a population of individuals not having a disorder of the immune system. As will be appreciated in the art, once a standard antimicrobial peptide level or mRNA level is known, it can be used repeatedly as a standard for comparison.

By "biological sample" is intended any biological sample obtained from an individual, body fluid, cell line, tissue culture, or other source which contains antimicrobial peptide protein or mRNA. As indicated, biological samples include body fluids (such as sera, plasma, urine, synovial fluid and spinal fluid) which contain free antimicrobial peptide, immune system tissue, and other tissue sources found to express complete or mature antimicrobial peptide or a antimicrobial peptide receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include inflammatory and infectious conditions and any disregulation of immnune cell function.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the antimicrobial peptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying antimicrobial peptide levels in a biological sample can occur using antibody-based techniques. For example, antimicrobial peptide expression in tissues can be studied with classical immunohistological methods (Jalkanen, M., et al., *J. Cell. Biol.* 101:976–985 (1985); Jalkanen, M., et al., *J. Cell . Biol.* 105:3087–3096 (1987)). Other antibody-based methods useful for detecting antimicrobial peptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{112}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying antimicrobial peptide levels in a biological sample obtained from an individual, antimicrobial peptide can also be detected in vivo by imaging. Antibody labels or markers for in vivo imaging of antimicrobial peptide include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A antimicrobial peptide-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain antimicrobial peptide. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer,* S. W. Burchiel and B. A. Rhodes, eds., Masson Publishing Inc. (1982)).

Therapeutics

The antimicrobial peptide of the present invention can be used as an antimicrobial agent for the treatment of fungal or bacterial infections. The peptide of the present invention can be used for such treatment in a topical or systemic formulation for the treatment of acne, burns, eye infections, mouthwash, deodorant or topical fungicides. In addition, *C. albicans,* the common cause of mucocutaneous fungal disease in AIDS patients, which is extremely susceptible to several β-defensins, might be controlled in these individuals more effectively by a β-defensin-based therapeutic or in combination with existing drugs.

Modes of administration

It will be appreciated that conditions caused by a decrease in the standard or normal level of antimicrobial peptide activity in an individual, can be treated by administration of antimicrobial peptide. Thus, the invention further provides a method of treating an individual in need of an increased level of antimicrobial peptide activity comprising administering to such an individual a pharmaceutical composition comprising an effective amount of an isolated antimicrobial peptide of the invention, particularly a mature form of the antimicrobial peptide, effective to increase the antimicrobial peptide activity level in such an individual.

As a general proposition, the total pharmaceutically effective amount of antimicrobial peptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the antimicrobial peptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed.

Pharmaceutical compositions containing the antimicrobial peptide of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a antimicrobial peptide gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as -short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of Antimicrobial peptide in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amps") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6× His tag") covalently linked to the carboxyl terminus of that polypeptide.

The DNA sequence encoding the desired portion the human antimicrobial peptide lacking the hydrophobic leader sequence is amplified from the deposited cDNA clone using PCR oligonucleotide primers which anneal to the amino terminal sequences of the desired portion of the human antimicrobial peptide and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence 5'GACT CCATGGGTGTTTTTGGTGGTATAGGC 3'(SEQ ID NO:6) containing the underlined NcoI restriction site followed by 20 nucleotides complementary to the amino terminal coding sequence of the mature human antimicrobial peptide sequence in FIG. 1. one of ordinary skill in the art would appreciate, of course, that the point in the protein coding sequence where the 5' primer begins may be varied to amplify a DNA segment encoding any desired portion of the complete protein shorter or longer than the mature form. The 3' primer has the sequence 5'GACT AGATCTTGGCTTTTTGCAGCATTTTG 3'(SEQ ID NO:7) containing the underlined BglII restriction site followed by 20 nucleotides complementary to the 3' end of the coding sequence immediately before the stop codon in the human antimicrobial peptide DNA sequence in FIG. 1, with the coding sequence aligned with the restriction site so as to maintain its reading frame with that of the six His codons in the pQE60 vector.

The amplified human antimicrobial peptide DNA fragment and the vector pQE60 are digested with NcoI and BglII and the digested DNAs are then ligated together. Insertion of the human antimicrobial peptide DNA into the restricted pQE60 vector places the human antimicrobial peptide protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing human antimicrobial peptide, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the human antimicrobial peptide is loaded onto a nickel-nitrilo-tri-acetic acid ("Ni-NTA") affinity resin column (available from QIAGEN, Inc., supra). Proteins with a 6× His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the human antimicrobial peptide is eluted with 6 M guanidine-HCl, pH5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH6 buffer plus 200 mM NaCl. The purified protein is stored at 4° C. or frozen at −80° C.

Example 1(b)

Expression and Purification of Antimicrobial Peptide in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6× His tag") covalently linked to the carboxyl terminus of that polypeptide. However, in this example, the polypeptide coding sequence is inserted such that translation of the six His codons is prevented and, therefore, the polypeptide is produced with no 6× His tag.

The DNA sequence encoding the desired portion of the mature human antimicrobial peptide lacking the hydrophobic leader sequence is amplified from the deposited cDNA clone using PCR oligonucleotide primers which anneal to the amino terminal sequences of the desired portion of the human antimicrobial peptide and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence 5'GACT CCATGGGTGTTTTTGGTGGTATAGGC 3'(SEQ ID NO:6) containing the underlined NcoI restriction site followed by 20 nucleotides complementary to the amino terminal coding sequence of the mature human antimicrobial peptide sequence in FIG. 1. One of ordinary skill in the art would appreciate, of course, that the point in the protein coding sequence where the 5' primer begins may be varied to amplify a desired portion of the complete protein shorter or longer than the mature form. The 3' primer has the sequence 5'GACT AGATCTTCATGGCTTTTTGCAGCATTTTG 3'(SEQ ID NO:8) containing the underlined BglII restriction site followed by a stop codon and 20 nucleotides complementary to the 3' end of the coding sequence in the human antimicrobial peptide DNA sequence in FIG. 1.

The amplified human antimicrobial peptide DNA fragments and the vector pQE60 are digested with NcoI and BglII and the digested DNAs are then ligated together. Insertion of the human antimicrobial peptide DNA into the restricted pQE60 vector places the human antimicrobial peptide protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing human antimicrobial peptide, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:25 to 1:250. The cells are grown to an optical density at 600 nm ("OD600") of between 0.4 and 0.6. Isopropyl-b-D- thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the human antimicrobial peptide is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure human antimicrobial peptide. The purified protein is stored at 4° C. or frozen at -80° C.

Example 2

Cloning and Expression of Antimicrobial Peptide in a Baculovirus Expression System In this illustrative example, the plasmid shuttle vector pA2 is used to insert the cloned DNA encoding the complete protein, including its naturally associated secretary signal (leader) sequence, into a baculovirus to express the mature human antimicrobial peptide, using standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHII and Asp718. The polyadenylation site of the simian virus 40 (" SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the full length human antimicrobial peptide protein in the deposited clone, including the AUG initiation codon and the naturally associated leader sequence shown in FIG. 1 (SEQ ID NO:2), is amplified using PCR oligonucleotide primers corresponding to the 5' and 3' sequences of the gene. The 5' primer has the sequence 5'GACT GGATCCGCCATCATGAGGGTCTTGTATCTCC 3'(SEQ ID NO:9) containing the underlined BamHI restriction enzyme site, an efficient signal for initiation of translation in eukaryotic cells, as described by Kozak, M., *J. Mol. Biol.* 196:947–950 (1987), followed by 19 bases of the sequence of the complete human antimicrobial peptide shown in FIG. 1, beginning with the AUG initiation codon. The 3' primer has the sequence 5'GACT GGTACCGATGTCGCACGTCTCTGATG 3'(SEQ ID NO:10) containing the underlined, Asp718 restriction site followed by 20 nucleotides complementary to the 3' non-coding sequence in FIG. 1.

The amplified fragment is isolated from a 1% agarose gel using a commercially available kit ("Geneclean," BIO 101 Inc., La Jolla, Calif.). The fragment then is digested with Bam HI and Asp718 and again is purified on a 1% agarose gel. This fragment is designated herein "F1".

The plasmid is digested with the restriction enzymes Bam HI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Cailf.) cells are transformed with the ligation mixture and spread on culture plates. Bacteria are identified that contain the plasmid with the human antimicrobial peptide gene using the PCR method, in which one of the primers that is used to amplify the gene and the second primer is from well within the vector so that only those bacterial colonies containing the human antimicrobial peptide gene fragment will show amplification of the DNA. The sequence of the cloned fragment is confirmed by DNA sequencing. This plasmid is designated herein pBacantimicrobial peptide.

Five µg of the plasmid pBac antimicrobial peptide is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 µg of BaculoGold™ virus DNA and 5 µg of the plasmid pBac antimicrobial peptide are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-antimicrobial peptide.

To verify the expression of the human antimicrobial peptide gene, Sf9 cells are grown in Grace's medium supplemented with 10% heat inactivated FBS. The cells are infected with the recombinant baculovirus V-antimicrobial peptide at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of Human Antimicrobial Peptide in Mammalian Cells

A typical mammalian expression vector contains the promoter element, which mediates the initiation oftranscription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 22 7:277–279 (199 1); Bebbington et al., *Bio/Technology* 10: 169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the 4; -production of proteins.

The expression vectors pC 1 and pC4 contain the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pAntimicrobial HA, is made by cloning a cDNA encoding the full length human antimicrobial peptide into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the -4 influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the full length antimicrobial peptide is cloned into the polylinker region of the vector so that recombinant protein expression is directed by the CMV promoter. The plasmid construction strategy is as follows. The antimicrobial peptide cDNA of the deposited clone is amplified using primers that contain convenient restriction sites, much as described above for construction of vectors for expression of antimicrobial peptide in *E. coli*. Suitable primers include the following, which are used in this example. The 5' primer, containing the underlined BamHI site, a Kozak sequence, an AUG start codon and 19 nucleotides of the 5' coding region of the complete antimicrobial peptide has the following sequence: 5'GACT <u>GGATCC</u>GCCATCATGAGGGTCTTGTATCTCC 3'(SEQ ID NO:9). The 3' primer, containing the underlined BglII site, and 20 bp of 3' coding sequence has the following sequence (at the 3' end): 5'GACT <u>AGATCT</u>TGGCTTTTTGCAGCATTTTG 3'(SEQ ID NO:7).

The PCR amplified DNA fragment and the vector, pcDNAI/Amp, are digested with BamHI and BglII and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the antimicrobial peptide encoding fragment.

For expression of recombinant antimicrobial peptide, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of antimicrobial peptide by the vector.

Expression of the antimicrobial peptide-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of antimicrobial peptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the antimicrobial peptide in a regulated way in mammalian cells (Gossen, M., & Bujard, H. 1992, *Proc. Natl. Acad. Sci. USA* 89: 5547–5551). For the polyadenylation of the MRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete antimicrobial peptide including its leader sequence is amplified using PCR oligonucleotide primers corresponding to the 5' and 3' sequences of the gene. The 5' primer has the sequence 5' GACTGGATCCGCCATCATGAGGGTCTTGTATCTCC3'(SEQ ID NO:9) containing the underlined BamHI restriction enzyme site followed by an efficient signal for initiation of translation in eukaryotes, as described by Kozak, M., *J. Mol. Biol.* 196:947–950 (1987), and 20 bases of the coding sequence of antimicrobial peptide shown in FIG. 1 (SEQ ID NO: 1). The 3' primer has the sequence 5'GACT GGTACCGATGTCGCACGTCTCTGATG 3'(SEQ ID NO: 10) containing the underlined Asp718 restriction site followed by 20 nucleotides complementary to the non-translated region of the antimicrobial peptide gene shown in FIG. 1 (SEQ ID NO: 1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reverse phase HPLC analysis.

Example 4

Tissue distribution of Antimicrobial peptide mRNA expression

Northern blot analysis is carried out to examine antimicrobial peptide gene expression in human tissues, using methods described by, among others, Sambrook et al., cited above. A cDNA probe containing the entire nucleotide sequence of the antimicrobial peptide (SEQ ID NO: 1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for antimicrobial peptide mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleic acid at least 95% identical to a reference nucleic acid encoding amino acids 1 to 41 of SEQ ID NO:2, wherein % identity is determined using the Bestfit program with parameters that calculate % identity over the full length of said reference nucleic acid and that allow gaps of up to 5% of the total number of nucleotides of said reference nucleic acid.

2. The isolated polynucleotide of claim 1, wherein said reference nucleic acid is nucleotides 105 to 227 of SEQ ID NO: 1.

3. The isolated polynucleotide of claim 1, wherein said reference nucleic acid encodes amino acids −22 to 41 of SEQ ID NO:2.

4. The isolated polynucleotide of claim 3, wherein said reference nucleic acid is nucleotides 39 to 227 of SEQ ID NO: 1.

5. The isolated polynucleotide of claim 3, wherein said reference nucleic acid encodes amino acids −23 to 41 of SEQ ID NO:2.

6. The isolated polynucleotide of claim 5, wherein said reference nucleic acid is nucleotides 36 to 227 of SEQ ID NO: 1.

7. The isolated polynucleotide of claim 1, further comprising a heterologous polynucleotide.

8. A method of producing a vector comprising inserting the isolated polynucleotide of claim 1 into a vector.

9. A vector comprising the isolated polynucleotide of claim 1.

10. The vector of claim 9, wherein said isolated polynucleotide is operably associated with a heterologous regulatory sequence.

11. A host cell comprising the isolated polynucleotide of claim 1.

12. The host cell of claim 11, wherein said isolated polynucleotide is operably associated with a heterologous regulatory sequence.

13. A method of producing a polypeptide comprising culturing the host cell of claim 12 under conditions such that a polypeptide is expressed, and recovering said polypeptide.

14. A composition comprising the isolated polynucleotide of claim 1.

15. An isolated polynucleotide comprising a nucleic acid at least 95% identical to a reference nucleic acid encoding the mature amino acid sequence encoded by the cDNA clone in ATCC Deposit No. 97982, wherein % identity is determined using the Bestfit program with parameters that calculate % identity over the full length of said reference nucleic acid and that allow gaps of up to 5% of the total number of nucleotides of said reference nucleic acid.

16. The isolated polynucleotide of claim 15, wherein said reference nucleic acid is the coding region of the cDNA clone in ATCC Deposit No. 97982.

17. The isolated polynucleotide of claim 15, further comprising a heterologous polynucleotide.

18. A method of producing a vector comprising inserting the isolated polynucleotide of claim 15 into a vector.

19. A vector comprising the isolated polynucleotide of claim 15.

20. The vector of claim 19, wherein said isolated polynucleotide is operably associated with a heterologous regulatory sequence.

21. A host cell comprising the isolated polynucleotide of claim 15.

22. The host cell of claim 21, wherein said isolated polynucleotide is operably associated with a heterologous regulatory sequence.

23. A method of producing apolypeptide comprising culturing the host cell of claim 22 under conditions such that a polypeptide is expressed, and recovering said polypeptide.

24. A composition comprising the isolated polynucleotide of claim 15.

25. An isolated polynucleotide comprising a nucleic acid encoding an amino acid sequence at least 95% identical to amino acids 1 to 41 of SEQ ID NO:2 (the reference sequence), wherein % identity is determined using the Bestfit program with parameters that calculate % identity over the full length of said reference sequence and that allow gaps of up to 5% of the total number of residues of said reference sequence.

26. The isolated polynucleotide of claim 25, wherein said reference sequence is amino acids −22 to 41 of SEQ ID NO:2.

27. The isolated polynucleotide of claim 25, wherein said reference sequence is amino acids −23 to 41 of SEQ ID NO:2.

28. The isolated polynucleotide of claim 25, further comprising a heterologous polynucleotide.

29. A method of producing a vector comprising inserting the isolated polynucleotide of claim 25 into a vector.

30. A vector comprising the isolated polynucleotide of claim 25.

31. The vector of claim 30, wherein said isolated polynucleotide is operably associated with a heterologous regulatory sequence.

32. A host cell comprising the isolated polynucleotide of claim 25.

33. The host cell of claim 32, wherein said isolated polynucleotide is operably associated with a heterologous regulatory sequence.

34. A method of producing a polypeptide comprising culturing the host cell of claim 33 under conditions such that a polypeptide is expressed, and recovering said polypeptide.

35. A composition comprising the isolated polynucleotide of claim 25.

36. An isolated polynucleotide comprising a nucleic acid encoding an amino acid sequence at least 95% identical to the mature amino acid sequence encoded by the cDNA clone in ATCC Deposit No. 97982 (the reference sequence), wherein % identity is determined using the Bestfit program with parameters that calculate % identity over the full length of said reference sequence and that allow gaps of up to 5% of the total number of residues of said reference sequence.

37. The isolated polynucleotide of claim 36, wherein said amino acid sequence is at least 95% identical to the complete amino acid sequence encoded by the cDNA clone in ATCC Deposit No. 97982.

38. The isolated polynucleotide of claim 36, further comprising a heterologous polynucleotide.

39. A method of producing a vector comprising inserting the isolated polynucleotide of claim 36 into a vector.

40. A vector comprising the isolated polynucleotide of claim 36.

41. The vector of claim 40, wherein said isolated polynucleotide is operably associated with a heterologous regulatory sequence.

42. A host cell comprising the isolated polynucleotide of claim 36.

43. The host cell of claim 42, wherein said isolated polynucleotide is operably associated with a heterologous regulatory sequence.

44. A method of producing a polypeptide comprising culturing the host cell of claim 43 under conditions such that a polypeptide is expressed, and recovering said polypeptide.

45. A composition comprising the isolated polynucleotide of claim 36.

46. An isolated polynucleotide comprising a nucleic acid encoding a fragment of SEQ ID NO:2, wherein said fragment exhibits antimicrobial activity.

47. The isolated polynucleotide of claim 46, further comprising a heterologous polynucleotide.

48. A method of producing a vector comprising inserting the isolated polynucleotide of claim 46 into a vector.

49. A vector comprising the isolated polynucleotide of claim 46.

50. The vector of claim 49, wherein said isolated polynucleotide is operably associated with a heterologous regulatory sequence.

51. A host cell comprising the isolated polynucleotide of claim 46.

52. The host cell of claim 51, wherein said isolated polynucleotide is operably associated with a heterologous regulatory sequence.

53. A method of producing a polypeptide comprising culturing the host cell of claim 52 under conditions such that a polypeptide is expressed, and recovering said polypeptide.

54. A composition comprising the isolated polynucleotide of claim 46.

55. An isolated polynucleotide comprising a nucleic acid encoding a fragment of the amino acid sequence encoded by the cDNA clone in ATCC Deposit No. 97982, wherein said fragment exhibits antimicrobial activity.

56. The isolated polynucleotide of claim 55, further comprising a heterologous polynucleotide.

57. A method of producing a vector comprising inserting the isolated polynucleotide of claim 55 into a vector.

58. A vector comprising the isolated polynucleotide of claim 55.

59. The vector of claim 58, wherein said isolated polynucleotide is operably associated with a heterologous regulatory sequence.

60. A host cell comprising the isolated polynucleotide of claim 55.

61. The host cell of claim 60, wherein said isolated polynucleotide is operably associated with a heterologous regulatory sequence.

62. A method of producing a polypeptide comprising culturing the host cell of claim 61 under conditions such that a polypeptide is expressed, and recovering said polypeptide.

63. A composition comprising the isolated polynucleotide of claim 55.

64. An isolated polynucleotide comprising a nucleic acid encoding the mature amino acid sequence encoded by the cDNA clone in ATCC Deposit No. 97982.

65. The isolated polynucleotide of claim 64, comprising a nucleic acid encoding the complete amino acid sequence encoded by the cDNA clone in ATCC Deposit No. 97982.

66. The isolated polynucleotide of claim 64, comprising the coding region of the cDNA clone in ATCC Deposit No. 97982.

67. The isolated polynucleotide of claim 64, further comprising a heterologous polynucleotide.

68. A method of producing a vector comprising inserting the isolated polynucleotide of claim 64 into a vector.

69. A vector comprising the isolated polynucleotide of claim 64.

70. The vector of claim 69, wherein said isolated polynucleotide is operably associated with a heterologous regulatory sequence.

71. A host cell comprising the isolated polynucleotide of claim 64.

72. The host cell of claim 71, wherein said isolated polynucleotide is operably associated with a heterologous regulatory sequence.

73. A method of producing a polypeptide comprising culturing the host cell of claim 72 under conditions such that a polypeptide is expressed, and recovering said polypeptide.

74. A composition comprising the polynucleotide of claim 64.

75. An isolated polynucleotide comprising a nucleic acid encoding amino acids 1 to 41 of SEQ ID NO:2.

76. The isolated polynucleotide of claim 75, comprising a nucleic acid encoding amino acids −22 to 41 of SEQ ID NO:2.

77. The isolated polynucleotide of claim 76, comprising a nucleic acid encoding amino acids −23 to 41 of SEQ ID NO:2.

78. The isolated polynucleotide of claim 75, further comprising a heterologous polynucleotide.

79. A method of producing a vector comprising inserting the isolated polynucleotide of claim 75 into a vector.

80. A vector comprising the isolated polynucleotide of claim 75.

81. The vector of claim 80, wherein said isolated polynucleotide is operably associated with a heterologous regulatory sequence.

82. A host cell comprising the isolated polynucleotide of claim 75.

83. The host cell of claim 82, wherein said isolated polynucleotide is operably associated with a heterologous regulatory sequence.

84. A method of producing a polypeptide comprising culturing the host cell of claim 83 under conditions such that a polypeptide is expressed, and recovering said polypeptide.

85. A composition comprising the polynucleotide of claim 75.

86. The complement of the isolated polynucleotide of claim 1.

87. The complement of the isolated polynucleotide of claim 15.

88. The complement of the isolated polynucleotide of claim 25.

89. The complement of the isolated polynucleotide of claim 36.

90. The complement of the isolated polynucleotide of claim 36.

91. The complement of the isolated polynucleotide of claim 55.

92. The complement of the isolated polynucleotide of claim 64.

93. The complement of the isolated polynucleotide of claim 75.

94. An isolated polynucleotide comprising a nucleic acid selected from the group consisting of:
(a) a nucleic acid encoding amino acids 19 to 27 of SEQ ID NO:2; and
(b) a nucleic acid encoding amino acids 31 to 41 of SEQ ID NO:2.

95. The isolated polynucleotide of claim 94, wherein said nucleic acid is (a).

96. The isolated polynucleotide of claim 94, wherein said nucleic acid is (b).

97. An isolated nucleic acid molecule comprising a first polynucleotide which hybridizes (i) at 42° C. in 50% formamide, 5× SSC, 50 mM sodium phosphate, 5× Denhardt's solution, 10% dextran sulfate, and 20 μg/ml denatured, sheared salmon sperm DNA; (ii) in a wash solution consisting of 0.1× SSC at 65° C.; to a second polynucleotide selected from the group consisting of:
(a) a polynucleotide having the sequence of the coding region of the cDNA clone contained in ATCC Deposit No. 97982 or the complement thereof; and
(b) a polynucleotide having the sequence of the coding region of SEQ ID NO: 1 or the complement thereof.

98. The isolated polynucleotide of claim 97, further comprising a heterologous polynucleotide.

99. A method of producing a vector comprising inserting the isolated polynucleotide of claim 97 into a vector.

100. A vector comprising the isolated polynucleotide of claim 97.

101. The vector of claim 100, wherein said isolated polynucleotide is operably associated with a heterologous regulatory sequence.

102. A host cell comprising the isolated polynucleotide of claim 97.

103. The host cell of claim 102, wherein said isolated polynucleotide is operably associated with a heterologous regulatory sequence.

104. An isolated polynucleotide comprising a nucleic acid encoding 30 or more contiguous amino acids of SEQ ID NO:2.

105. The isolated polynucleotide of claim 104, wherein said polynucleotide encodes 50 or more contiguous amino acids of SEQ ID NO:2.

106. The isolated polynucleotide of claim 104, further comprising a heterologous polynucleotide.

107. A method of producing a vector comprising inserting the isolated polynucleotide of claim 104 into a vector.

108. A vector comprising the isolated polynucleotide of claim 104.

109. The vector of claim 108, wherein said isolated polynucleotide is operably associated with a heterologous regulatory sequence.

110. A host cell comprising the isolated polynucleotide of claim 104.

111. The host cell of claim 110, wherein said isolated polynucleotide is operably associated with a heterologous regulatory sequence.

112. A method of producing a polypeptide comprising culturing the host cell of claim 111 under conditions such that a polypeptide is expressed, and recovering said polypeptide.

113. A composition comprising the isolated polynucleotide of claim 104.

114. An isolated polynucleotide comprising 30 contiguous nucleotides of the coding region of SEQ ID NO:1.

115. The isolated polynucleotide of claim 114, which comprises 50 contiguous nucleotides of the coding region of SEQ ID NO: 1.

116. The isolated polynucleotide of claim 114, further comprising a heterologous polynucleotide.

117. A method of producing a vector comprising inserting the isolated polynucleotide of claim 114 into a vector.

118. A vector comprising the isolated polynucleotide of claim 114.

119. The vector of claim 118, wherein said isolated polynucleotide is operably associated with a heterologous regulatory sequence.

120. A host cell comprising the isolated polynucleotide of claim 114.

121. The host cell of claim 120, wherein said isolated polynucleotide is operably associated with a heterologous regulatory sequence.

122. A composition comprising the isolated polynucleotide of claim 114.

* * * * *

UNITED STATES PATENT AND TRADEMARK OFFICE
CERTIFICATE OF CORRECTION

PATENT NO. : 6,143,498
DATED : November 7, 2000
INVENTOR(S) : Olsen et al.

It is certified that error appears in the above-identified patent and that said Letters Patent is hereby corrected as shown below:

Column 39,
Line 22 at claim 23, please delete "apolypeptide" and insert therein --a polypeptide--.

Column 42,
Line 2 at claim 90, please delete "36" and insert therein --46--.
Line 20 at claim 97, please delete "C." and insert therein --C--; and
Line 25, please delete "C." and insert therein --C--.

Signed and Sealed this

Nineteenth Day of June, 2001

*Attest:*

NICHOLAS P. GODICI
*Attesting Officer*       *Acting Director of the United States Patent and Trademark Office*

```
                        SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 323 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 36..227

(ix) FEATURE:
        (A) NAME/KEY: sig_peptide
        (B) LOCATION: 36..104

(ix) FEATURE:
        (A) NAME/KEY: mat_peptide
        (B) LOCATION: 105..227

(xi) SEQUENCE DESCRIPTION: SEQ ID NO:1:

GACTCAGCTC CTGGTGAAGC TCCCAGCCAT CAGCC ATG AGG GTC TTG TAT CTC          53
                                      Met Arg Val Leu Tyr Leu
                                      -23               -20

CTC TTC TCG TTC CTC TTC ATA TTC CTG ATG CCT CTT CCA GGT GTT TTT       101
Leu Phe Ser Phe Leu Phe Ile Phe Leu Met Pro Leu Pro Gly Val Phe
            -15                 -10                  -5

GGT GGT ATA GGC GAT CCT GTT ACC TGC CTT AAG AGT GGA GCC ATA TGT       149
Gly Gly Ile Gly Asp Pro Val Thr Cys Leu Lys Ser Gly Ala Ile Cys
  1               5                  10                       15

CAT CCA GTC TTT TGC CCT AGA AGG TAT AAA CAA ATT GGC ACC TGT GGT       197
His Pro Val Phe Cys Pro Arg Arg Tyr Lys Gln Ile Gly Thr Cys Gly
                20                  25                  30

CTC CCT GGA ACA AAA TGC TGC AAA AAG CCA TGAGGAGGCC AAGAAGCTGC         247
Leu Pro Gly Thr Lys Cys Cys Lys Lys Pro
                35                  40

TGTGGCTGAT GCGGATTCAG AAAGGGCTCC CTCATCAGAG ACGTGCGACA TGTAAACCAA     307

ATTAAACTAT GGTGTC                                                     323
```

(2) INFORMATION FOR SEQ ID NO:2:

(i) SEQUENCE CHARACTERISTICS:
  (A) LENGTH: 64 amino acids
  (B) TYPE: amino acid
  (D) TOPOLOGY: linear (ii) MOLECULE TYPE: protein (xi) SEQUENCE DESCRIPTION: SEQ ID NO:2:

```
Met Arg Val Leu Tyr Leu Leu Phe Ser Phe Leu Phe Ile Phe Leu Met
-23         -20             -15             -10

Pro Leu Pro Gly Val Phe Gly Gly Ile Gly Asp Pro Val Thr Cys Leu
         -5              1               5

Lys Ser Gly Ala Ile Cys His Pro Val Phe Cys Pro Arg Arg Tyr Lys
10              15              20              25

Gln Ile Gly Thr Cys Gly Leu Pro Gly Thr Lys Cys Cys Lys Lys Pro
            30              35              40
```

(2) INFORMATION FOR SEQ ID NO:3:

(i) SEQUENCE CHARACTERISTICS:
  (A) LENGTH: 63 amino acids
  (B) TYPE: amino acid
  (C) STRANDEDNESS: single
  (D) TOPOLOGY: Not Relevant (ii) MOLECULE TYPE: peptide (xi) SEQUENCE DESCRIPTION: SEQ ID NO:3:

```
Met Arg Leu His His Leu Leu Leu Ala Leu Leu Phe Leu Val Leu Ser
1               5               10              15

Ala Trp Ser Gly Phe Thr Gln Gly Val Gly Asn Pro Val Ser Cys Val
            20              25              30

Arg Asn Lys Gly Ile Cys Val Pro Ile Arg Cys Pro Gly Ser Met Lys
        35              40              45

Gln Ile Gly Thr Cys Val Gly Arg Ala Val Lys Cys Cys Arg Lys
    50              55              60
```

(2) INFORMATION FOR SEQ ID NO:4:

(i) SEQUENCE CHARACTERISTICS:
  (A) LENGTH: 3974 base pairs
  (B) TYPE: nucleic acid
  (C) STRANDEDNESS: both
  (D) TOPOLOGY: both (ii) MOLECULE TYPE: cDNA (xi) SEQUENCE DESCRIPTION: SEQ ID NO:4:

```
GGTACCTAAG TGAGTAGGGC GTCCGATCGA CGGACGCCTT TTTTTTGAAT TCGTAATCAT      60

GGTCATAGCT GTTTCCTGTG TGAAATTGTT ATCCGCTCAC AATTCCACAC AACATACGAG     120

CCGGAAGCAT AAAGTGTAAA GCCTGGGGTG CCTAATGAGT GAGCTAACTC ACATTAATTG     180

CGTTGCGCTC ACTGCCCGCT TTCCAGTCGG GAAACCTGTC GTGCCAGCTG CATTAATGAA     240

TCGGCCAACG CGCGGGGAGA GGCGGTTTGC GTATTGGGCG CTCTTCCGCT TCCTCGCTCA     300

CTGACTCGCT GCGCTCGGTC GTTCGGCTGC GGCGAGCGGT ATCAGCTCAC TCAAAGGCGG     360

TAATACGGTT ATCCACAGAA TCAGGGGATA ACGCAGGAAA GAACATGTGA GCAAAAGGCC     420

AGCAAAAGGC CAGGAACCGT AAAAAGGCCG CGTTGCTGGC GTTTTTCCAT AGGCTCCGCC     480
```

-continued

```
CCCCTGACGA GCATCACAAA AATCGACGCT CAAGTCAGAG GTGGCGAAAC CCGACAGGAC    540

TATAAAGATA CCAGGCGTTT CCCCCTGGAA GCTCCCTCGT GCGCTCTCCT GTTCCGACCC    600

TGCCGCTTAC CGGATACCTG TCCGCCTTTC TCCCTTCGGG AAGCGTGGCG CTTTCTCATA    660

GCTCACGCTG TAGGTATCTC AGTTCGGTGT AGGTCGTTCG CTCCAAGCTG GGCTGTGTGC    720

ACGAACCCCC CGTTCAGCCC GACCGCTGCG CCTTATCCGG TAACTATCGT CTTGAGTCCA    780

ACCCGGTAAG ACACGACTTA TCGCCACTGG CAGCAGCCAC TGGTAACAGG ATTAGCAGAG    840

CGAGGTATGT AGGCGGTGCT ACAGAGTTCT TGAAGTGGTG GCCTAACTAC GGCTACACTA    900

GAAGAACAGT ATTTGGTATC TGCGCTCTGC TGAAGCCAGT TACCTTCGGA AAAAGAGTTG    960

GTAGCTCTTG ATCCGGCAAA CAAACCACCG CTGGTAGCGG TGGTTTTTTT GTTTGCAAGC   1020

AGCAGATTAC GCGCAGAAAA AAAGGATCTC AAGAAGATCC TTTGATCTTT TCTACGGGGT   1080

CTGACGCTCA GTGGAACGAA AACTCACGTT AAGGGATTTT GGTCATGAGA TTATCGTCGA   1140

CAATTCGCGC GCGAAGGCGA AGCGGCATGC ATTTACGTTG ACACCATCGA ATGGTGCAAA   1200

ACCTTTCGCG GTATGGCATG ATAGCGCCCG GAAGAGAGTC AATTCAGGGT GGTGAATGTG   1260

AAACCAGTAA CGTTATACGA TGTCGCAGAG TATGCCGGTG TCTCTTATCA GACCGTTTCC   1320

CGCGTGGTGA ACCAGGCCAG CCACGTTTCT GCGAAAACGC GGGAAAAAGT GGAAGCGGCG   1380

ATGGCGGAGC TGAATTACAT TCCCAACCGC GTGGCACAAC AACTGGCGGG CAAACAGTCG   1440

TTGCTGATTG GCGTTGCCAC CTCCAGTCTG GCCCTGCACG CGCCGTCGCA AATTGTCGCG   1500

GCGATTAAAT CTCGCGCCGA TCAACTGGGT GCCAGCGTGG TGGTGTCGAT GGTAGAACGA   1560

AGCGGCGTCG AAGCCTGTAA AGCGGCGGTG CACAATCTTC TCGCGCAACG CGTCAGTGGG   1620

CTGATCATTA ACTATCCGCT GGATGACCAG GATGCCATTG CTGTGGAAGC TGCCTGCACT   1680

AATGTTCCGG CGTTATTTCT TGATGTCTCT GACCAGACAC CCATCAACAG TATTATTTTC   1740

TCCCATGAAG ACGGTACGCG ACTGGGCGTG GAGCATCTGG TCGCATTGGG TCACCAGCAA   1800

ATCGCGCTGT TAGCGGGCCC ATTAAGTTCT GTCTCGGCGC GTCTGCGTCT GGCTGGCTGG   1860

CATAAATATC TCACTCGCAA TCAAATTCAG CCGATAGCGG AACGGGAAGG CGACTGGAGT   1920

GCCATGTCCG GTTTTCAACA AACCATGCAA ATGCTGAATG AGGGCATCGT TCCCACTGCG   1980

ATGCTGGTTG CCAACGATCA GATGGCGCTG GGCGCAATGC GCGCCATTAC CGAGTCCGGG   2040

CTGCGCGTTG GTGCGGATAT CTCGGTAGTG GGATACGACG ATACCGAAGA CAGCTCATGT   2100

TATATCCCGC CGTTAACCAC CATCAAACAG GATTTTCGCC TGCTGGGGCA AACCAGCGTG   2160

GACCGCTTGC TGCAACTCTC TCAGGGCCAG GCGGTGAAGG GCAATCAGCT GTTGCCCGTC   2220

TCACTGGTGA AAAGAAAAAC CACCCTGGCG CCCAATACGC AAACCGCCTC TCCCCGCGCG   2280

TTGGCCGATT CATTAATGCA GCTGGCACGA CAGGTTTCCC GACTGGAAAG CGGGCAGTGA   2340

GCGCAACGCA ATTAATGTAA GTTAGCGCGA ATTGTCGACC AAAGCGGCCA TCGTGCCTCC   2400

CCACTCCTGC AGTTCGGGGG CATGGATGCG CGGATAGCCG CTGCTGGTTT CCTGGATGCC   2460

GACGGATTTG CACTGCCGGT AGAACTCCGC GAGGTCGTCC AGCCTCAGGC AGCAGCTGAA   2520

CCAACTCGCG AGGGGATCGA GCCCGGGGTG GGCGAAGAAC TCCAGCATGA GATCCCCGCG   2580

CTGGAGGATC ATCCAGCCGG CGTCCCGGAA AACGATTCCG AAGCCCAACC TTTCATAGAA   2640

GGCGGCGGTG GAATCGAAAT CTCGTGATGG CAGGTTGGGC GTCGCTTGGT CGGTCATTTC   2700

GAACCCCAGA GTCCCGCTCA GAAGAACTCG TCAAGAAGGC GATAGAAGGC GATGCGCTGC   2760

GAATCGGGAG CGGCGATACC GTAAAGCACG AGGAAGCGGT CAGCCCATTC GCCGCCAAGC   2820

TCTTCAGCAA TATCACGGGT AGCCAACGCT ATGTCCTGAT AGCGGTCCGC CACACCCAGC   2880
```

```
CGGCCACAGT CGATGAATCC AGAAAAGCGG CCATTTTCCA CCATGATATT CGGCAAGCAG    2940

GCATCGCCAT GGGTCACGAC GAGATCCTCG CCGTCGGGCA TGCGCGCCTT GAGCCTGGCG    3000

AACAGTTCGG CTGGCGCGAG CCCCTGATGC TCTTCGTCCA GATCATCCTG ATCGACAAGA    3060

CCGGCTTCCA TCCGAGTACG TGCTCGCTCG ATGCGATGTT TCGCTTGGTG GTCGAATGGG    3120

CAGGTAGCCG GATCAAGCGT ATGCAGCCGC CGCATTGCAT CAGCCATGAT GGATACTTTC    3180

TCGGCAGGAG CAAGGTGAGA TGACAGGAGA TCCTGCCCCG GCACTTCGCC CAATAGCAGC    3240

CAGTCCCTTC CCGCTTCAGT GACAACGTCG AGCACAGCTG CGCAAGGAAC GCCCGTCGTG    3300

GCCAGCCACG ATAGCCGCGC TGCCTCGTCC TGCAGTTCAT TCAGGGCACC GGACAGGTCG    3360

GTCTTGACAA AAAGAACCGG GCGCCCCTGC GCTGACAGCC GGAACACGGC GGCATCAGAG    3420

CAGCCGATTG TCTGTTGTGC CCAGTCATAG CCGAATAGCC TCTCCACCCA AGCGGCCGGA    3480

GAACCTGCGT GCAATCCATC TTGTTCAATC ATGCGAAACG ATCCTCATCC TGTCTCTTGA    3540

TCAGATCTTG ATCCCCTGCG CCATCAGATC CTTGGCGGCA AGAAAGCCAT CCAGTTTACT    3600

TTGCAGGGCT TCCCAACCTT ACCAGAGGGC GCCCCAGCTG GCAATTCCGG TTCGCTTGCT    3660

GTCCATAAAA CCGCCCAGTC TAGCTATCGC CATGTAAGCC CACTGCAAGC TACCTGCTTT    3720

CTCTTTGCGC TTGCGTTTTC CCTTGTCCAG ATAGCCCAGT AGCTGACATT CATCCGGGGT    3780

CAGCACCGTT TCTGCGGACT GGCTTTCTAC GTGTTCCGCT TCCTTTAGCA GCCCTTGCGC    3840

CCTGAGTGCT TGCGGCAGCG TGAAGCTTAA AAAACTGCAA AAAATAGTTT GACTTGTGAG    3900

CGGATAACAA TTAAGATGTA CCCAATTGTG AGCGGATAAC AATTTCACAC ATTAAAGAGG    3960

AGAAATTACA TATG                                                     3974

(2) INFORMATION FOR SEQ ID NO:5:

(i) SEQUENCE CHARACTERISTICS:
         (A) LENGTH: 112 base pairs
         (B) TYPE: nucleic acid
         (C) STRANDEDNESS: both
         (D) TOPOLOGY: both (ii) MOLECULE TYPE: cDNA (xi) SEQUENCE DESCRIPTION: SEQ ID NO:5:

AAGCTTAAAA AACTGCAAAA AATAGTTTGA CTTGTGAGCG GATAACAATT AAGATGTACC      60

CAATTGTGAG CGGATAACAA TTTCACACAT TAAAGAGGAG AAATTACATA TG             112

(2) INFORMATION FOR SEQ ID NO:6:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

GACTCCATGG GTGTTTTTGG TGGTATAGGC                                       30

(2) INFORMATION FOR SEQ ID NO:7:

(i) SEQUENCE CHARACTERISTICS:
         (A) LENGTH: 30 base pairs
         (B) TYPE: nucleic acid
         (C) STRANDEDNESS: single
         (D) TOPOLOGY: linear
```

```
        (ii) MOLECULE TYPE: cDNA (xi) SEQUENCE DESCRIPTION: SEQ ID NO:7:

GACTAGATCT TGGCTTTTTG CAGCATTTTG                                            30

(2) INFORMATION FOR SEQ ID NO:8:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

GACTAGATCT TCATGGCTTT TTGCAGCATT TTG                                        33

(2) INFORMATION FOR SEQ ID NO:9:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

GACTGGATCC GCCATCATGA GGGTCTTGTA TCTCC                                      35

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GACTGGTACC GATGTCGCAC GTCTCTGATG                                            30
```